United States Patent [19]
Vetter et al.

[11] Patent Number: 5,989,227
[45] Date of Patent: Nov. 23, 1999

[54] PREFILLED SYRINGE WITH STERILITY-PRESERVING CAP

[75] Inventors: Helmut Vetter, Ravensburg; Thomas Otto, Weingarten, both of Germany

[73] Assignee: Arzneimittel GmbH Apotheker Vetter & Co., Ravensburg, Germany

[21] Appl. No.: 09/195,738

[22] Filed: Nov. 19, 1998

[30] Foreign Application Priority Data

Nov. 11, 1997 [DE] Germany .................. 197 51 219

[51] Int. Cl.⁶ ........................................ A61M 5/00
[52] U.S. Cl. ................... 604/232; 604/233; 604/234; 604/256
[58] Field of Search ..................... 604/200, 201, 604/232–234, 256, 82

[56] References Cited

U.S. PATENT DOCUMENTS

| | | |
|---|---|---|
| 2,906,423 | 9/1959 | Sandhage . |
| 5,135,496 | 8/1992 | Vetter et al. ............ 604/111 |
| 5,320,603 | 6/1994 | Vetter . |
| 5,328,474 | 7/1994 | Raines ...................... 604/110 |
| 5,649,912 | 7/1997 | Petersom .................. 604/187 |
| 5,693,027 | 12/1997 | Hansen et al. ........... 604/232 |

FOREIGN PATENT DOCUMENTS

| | | |
|---|---|---|
| WO 94/03373 | 2/1994 | European Pat. Off. . |
| WO 96/40037 | 12/1996 | European Pat. Off. . |
| 1139441 | 2/1957 | France . |
| 195 37 163 | 1/1997 | Germany . |
| 621524 | 2/1981 | Switzerland . |

*Primary Examiner*—Wynn Wood Coggins
*Assistant Examiner*—Kevin C. Sirmons
*Attorney, Agent, or Firm*—Herbert Dubno; Andrew Wilford

[57] ABSTRACT

A medicament container has a body having an open mouth defining an axis, a pierceable plug engaged over and sealing the mouth, a ring engaged around the mouth and over the plug and formed with a hole through which an outer surface of the plug is exposed, and a cap engageable around the mouth over the ring and plug. The cap holds an elastomeric element bearing elastically through the hole against the plug outer surface.

5 Claims, 2 Drawing Sheets

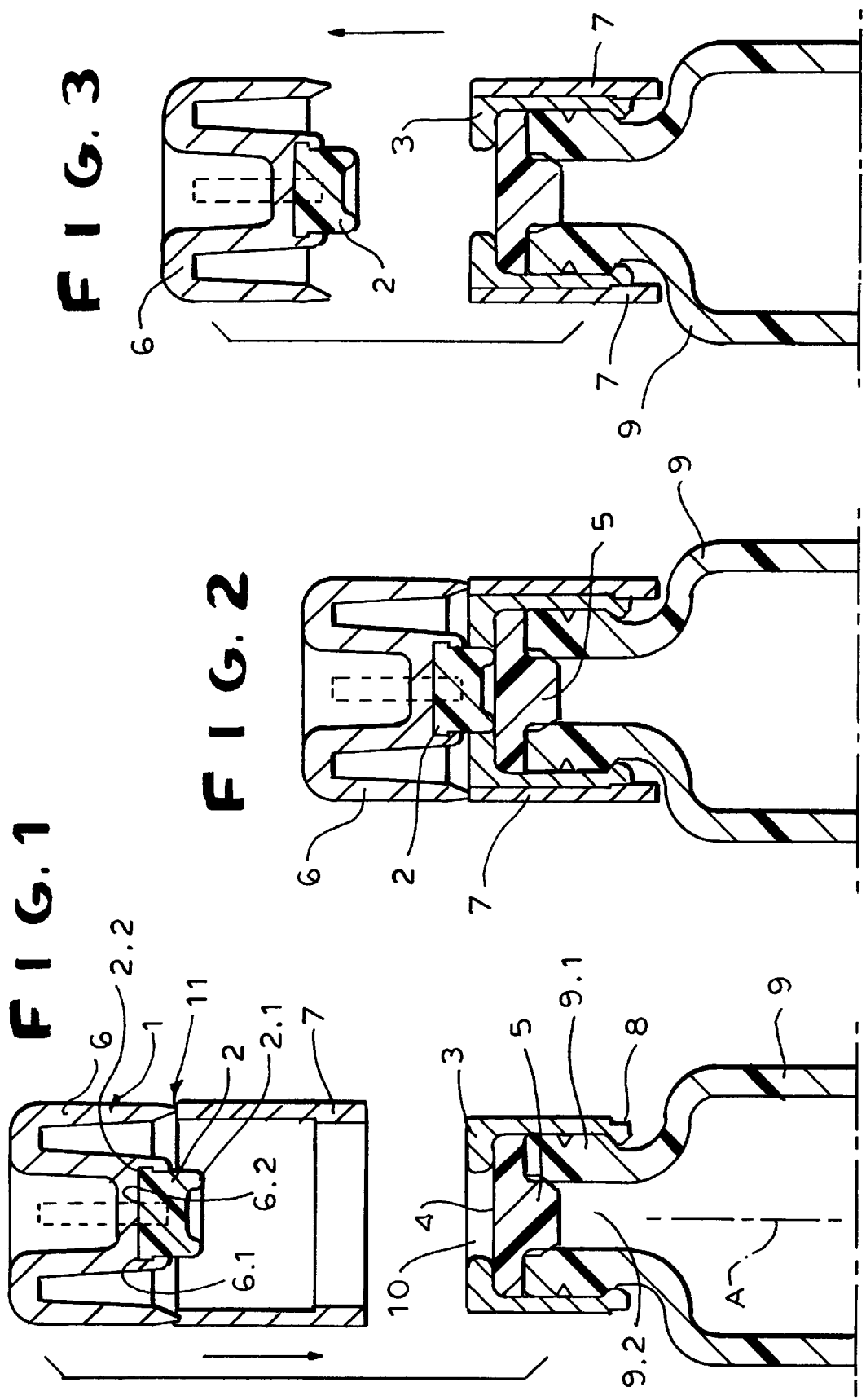

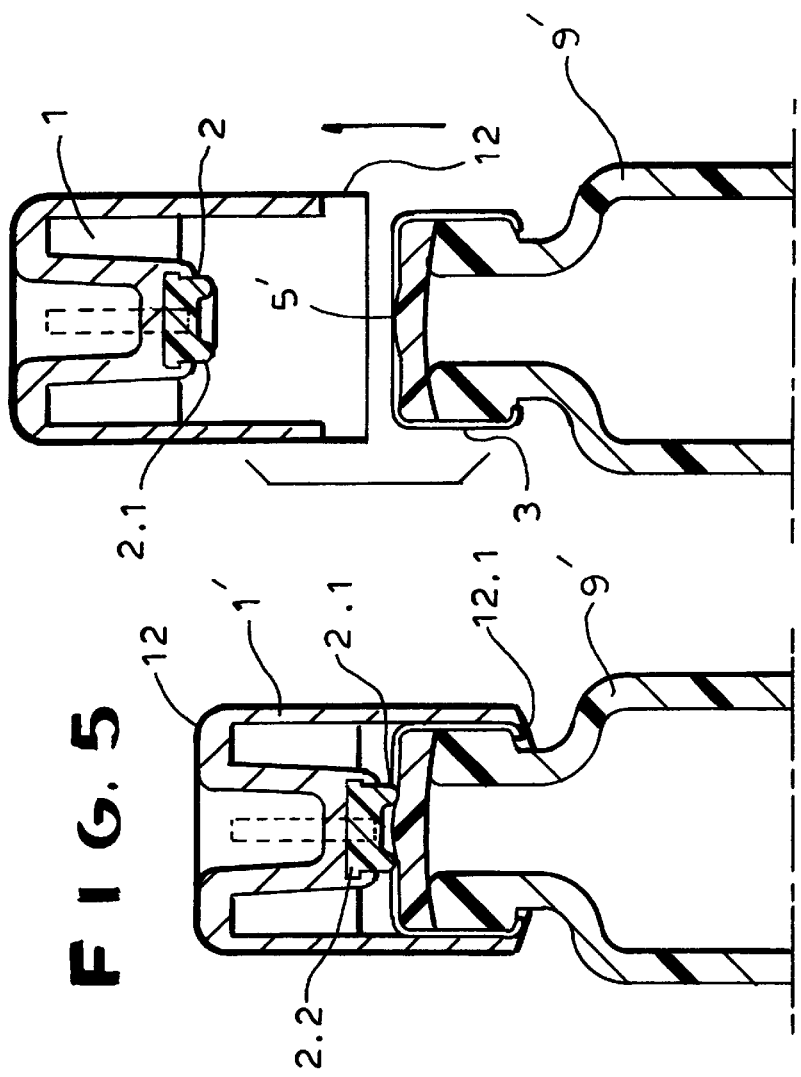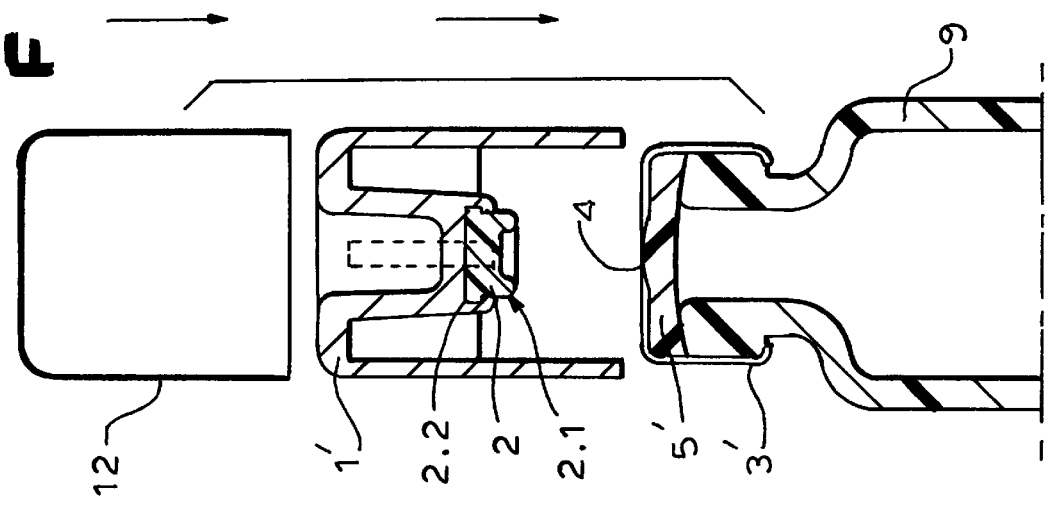

PREFILLED SYRINGE WITH STERILITY-PRESERVING CAP

FIELD OF THE INVENTION

The present invention relates to a prefilled syringe or carpule. More particularly this invention concerns such a prefilled medical container intended to be emptied by means of a needle inserted through its cap.

BACKGROUND OF THE INVENTION

A standard prefilled medicament container—a standard syringe or a so-called carpule® (Cook Laboratories Inc.)—has a hollow body having an open mouth defining an axis, a pierceable plug or membrane engaged over and sealing the mouth, a ring engaged around the mouth and over the plug and formed with a hole through which an outer surface of the plug is exposed, and a removable cap engageable around the mouth over the ring and plug. For use the cap is removed, the outer plug surface is cleaned, and a needle or cannula is poked through the plug. Then a piston in the body or other means is actuated to express the body's contents through the needle.

Cleaning the outer surface of the plug or membrane is necessary because the cap breathes somewhat and contaminants can get under it onto the surface. Such cleaning is relatively difficult, as the plug outer surface is recessed at the bottom of the hole in the retaining ring.

OBJECTS OF THE INVENTION

It is therefore an object of the present invention to provide an improved prefilled medicament container, that is syringe or carpule®.

Another object is the provision of such an improved prefilled medicament container which overcomes the above-given disadvantages, that is which does not require the user to clean the outer plug or membrane surface prior to poking the cannula through it.

SUMMARY OF THE INVENTION

A medicament container has according to the invention a body having an open mouth defining an axis, a pierceable plug engaged over and sealing the mouth, a ring engaged around the mouth and over the plug and formed with a hole through which an outer surface of the plug is exposed, and a cap engageable around the mouth over the ring and plug. In accordance with the invention the cap holds an elastomeric element bearing elastically through the hole against the plug outer surface.

Thus until the cap is removed, this elastomeric element completely prevents anything from getting to the sterile outer surface of the plug. There is therefore no need to clean it. The needle can be pushed through it without further preparation.

According to the invention the element is basically cylindrical and centered on the axis and is formed with an axially projecting annular ridge centered on the axis and engaging the plug outer surface. Furthermore the cap is formed with a seat in which the element is fitted. The element and seat are formed with radially interengaging formations retaining the element in the seat. In this manner the plug is solidly held in the cap. The formations include a radially outwardly projecting annular ridge on the plug and a radially inwardly open groove in the seat.

The cap in accordance with the invention includes an upper cap part carrying the element, a lower ring part fixed around the mouth of the body, and a weakened zone joining the lower and upper parts together so that the upper part can be easily broken off the lower part at the weakened zone. Alternately a shrink foil is engaged over the cap and around the mouth to retain the cap on the body. Both these systems give ample warning of tampering with the container to a potential user.

BRIEF DESCRIPTION OF THE DRAWING

The above and other objects, features, and advantages will become more readily apparent from the following description, reference being made to the accompanying drawing in which:

FIG. 1 is a side exploded sectional view of a syringe according to the invention;

FIG. 2 is a similar sectional view of the syringe of FIG. 1 in fully assembled condition;

FIG. 3 is a view like FIG. 2 but with the sterility-preserving cap removed for emptying of the syringe;

FIG. 4 is a view like FIG. 1 of a carpule® in accordance with the invention;

FIG. 5 is a view like FIG. 2 of the fully assembled carpule®; and

FIG. 6 is a view like FIG. 3 of the carpule® with its cap removed.

SPECIFIC DESCRIPTION

As seen in FIG. 1 a syringe according to the invention has a generally cylindrical hollow body 9 of glass or plastic having a small-diameter neck 9.1 with an opening 9.2 centered on an axis A. A standard pierceable elastomeric plug 5 is fitted to the end of the neck 9.1, extends into the opening 9.2, and has an outer face 4 extending in a plane perpendicular to the axis A. A retaining ring 3 of metal or plastic engaged around the neck 9.1 and over the outer edge of the surface 4 is formed centered on the axis A with a throughgoing hole 10 at which a center portion of the surface 4 is exposed. For use a sharp rear end of a cannula is inserted through the plug 5 and an unillustrated piston in the syringe 9 is advanced to express an unillustrated body of fluid medicament out through the cannula.

According to the invention a sterility-preserving cap 7 is employed which holds a cylindrical body 2 of soft elastomeric material of a diameter slightly smaller than the circular opening 10. This body 2 has an annular axially projecting ridge 2.1 centered on the axis A and engaging the surface 4 and a radially projecting ridge 2.2 that is engaged in a complementary groove 6.1 of a seat 6.2 formed in a cup-shaped part 6 constituting half of the cap 1. Another ring or collar 7 is joined at a weakened region 11 to the part 6 to form the rest of this cap 1.

Thus as shown in FIG. 2 prior to use the entire cap 1 sits atop the bottle 9 with the rim 2.1 in firm contact with the surface 4, maintaining its center perfectly clean and sterile. For use the part 6 carrying the body 2 is broken off at 11, leaving the ring 7 in place and exposing the sterile surface 4 as shown in FIG. 3.

In the arrangement of FIG. 4 of a carpule® 9' the plug 5' is held beneath a thin aluminum ring 3' so that its center bulges up a little. The cap 1' is of one piece and is held in place by a heat-shrunk cup-shaped plastic cover 12 that as shown in FIG. 5 reaches under the crimped ring 3' at a skirt 12.1. For use the cap 1' is physically lifted off as shown in FIG. 6, normally stretching and/or tearing the skirt 12.1.

In both systems the caps 1 and 1' not only serve to protect the sterility of the surface 4, but also act as tamper indicators in that neither of these caps 1 or 1' can be removed without making such removal obvious. These caps 1 and 1' cannot be removed and replaced without being permanently damaged.

We claim:

1. A medicament container comprising:

a body having an open mouth defining an axis;

a pierceable plug engaged over and sealing the mouth;

a ring engaged around the mouth and over the plug and formed with a hole through which an outer surface of the plug is exposed;

a cap engageable around the mouth over the ring and plug and including an upper cap part, a lower ring part fixed around the mouth of the body, and a weakened zone joining the lower and upper parts together, whereby the upper part can be easily broken off the lower part at the weakened zone; and an elastomeric element fixed in the upper cap part and bearing elastically through the hole against the plug outer surface.

2. The medicament container defined in claim 1 wherein the element is basically cylindrical and centered on the axis and is formed with an axially projecting annular ridge centered on the axis and engaging the plug outer surface.

3. The medicament container defined in claim 2 wherein the cap is formed with a seat in which the element is fitted, the element and seat being formed with radially interengaging formations retaining the element in the seat.

4. The medicament container defined in claim 3 wherein the formations include a radially outwardly projecting annular ridge on the plug and a radially inwardly open groove in the seat.

5. The medicament container defined in claim 1, further comprising a shrink foil engaged over the cap and around the mouth to retain the cap on the body.

\* \* \* \* \*